(12) United States Patent
Choi et al.

(10) Patent No.: US 6,649,382 B1
(45) Date of Patent: Nov. 18, 2003

(54) METHODS OF MAKING POLYHYDROXYALKANOATE USING BIOSYNTHESIS GENES FROM ALCALIGENES LATUS

(75) Inventors: Jong-il Choi, Seoul (KR); Sang Yup Lee, Taejon-si (KR); Kyuboem Han, Taejon-si (KR)

(73) Assignee: LG Chemical Ltd. (KR)

( * ) Notice: Subject to any disclaimer, the term of this patent is extended or adjusted under 35 U.S.C. 154(b) by 0 days.

(21) Appl. No.: 09/600,099
(22) PCT Filed: Jan. 19, 1999
(86) PCT No.: PCT/KR99/00031
§ 371 (c)(1), (2), (4) Date: Jul. 11, 2000
(87) PCT Pub. No.: WO99/36547
PCT Pub. Date: Jul. 22, 1999

(30) Foreign Application Priority Data

Jan. 19, 1998 (KR) .............................. 98-1422
Jan. 19, 1998 (KR) .............................. 98-1423
Dec. 26, 1998 (KR) .............................. 98-58760

(51) Int. Cl.$^7$ ................................. C12P 7/18
(52) U.S. Cl. ...................................... 435/158
(58) Field of Search ........................ 435/158

(56) References Cited

PUBLICATIONS

Kim et al. Enzymatic Characteristics of Biosynthesis and Degradation of Poly–beta–hydroxybutyrate of Alcaligenes latus. J. of Microbiol. Biotechnol. 1996;6(6):425–431.*

Choi et al. Cloning of the Alcaligenes latus polyhydroxyalkanoate biosynthesis genes and use of these genes for enhanced production of Poly(3–hydroxybutyrate) in *Escherichia coli*. Appl Environ Microbiol Dec. 2, 1998; 64(12):4897–903.*

Genser et al. Molecular cloning, sequencing and expression in *Escherichia coli* of the poly(3–hydroxyalkanoate) synthesis genes from Alcaligenes latus DSM 1124. J. of Biotechnol. Oct. 8, 1998;64:123–135.*

Hong et al. Alcaligenes latus poly–deta–hydroxybutyric acid synthase (phbC) gene, complete cds. GenBank Accession No. AF004933. Jan. 5, 1999.*

Ramsay et al. Production of poly–beta–hydroxybutyric–co–beta–hydroxyvaleric acids. Appl. Environ. Microbiol. Jul. 1990;56(7):2093–8.*

Schubert, Peter, *Cloning of the Alcaligenes eutrophus Genes for Synthesis of Poly–B–Hydroxybutyric Acid (PHB) and Synthesis of PHB in Escherichia coli*, Journal of Bacteriology, vol. 170, No. 12, Dec. 1988, p. 5837–5847.

Slater, Steven C., *Cloning and Expression in Escherichia coli of the Alcaligenes eutrophus H16 Poly–B–Hydroxybutyrate Biosynthetic Pathway*, Journal of Bacteriology, vol. 170, No. 10, Oct. 1988, p. 4431–4436.

Peoples, Oliver P., *Poly–B–hydroxybutyrate (PHB) Biosynthesis in Alcaligenes eutrophus H16*, The Journal of Biological Chemistry, vol. 264, No. 26, Sep. 15, 1989, pp. 15298–15303.

* cited by examiner

*Primary Examiner*—Ponnathapu Achutamurthy
*Assistant Examiner*—Kathleen Kerr
(74) *Attorney, Agent, or Firm*—Muserlian, Lucas and Mercanti, LLP

(57) ABSTRACT

There are described methods for making polyhydroxyalkanoate and its copolymers, by culturing a host cell transformed with a vector comprising a polyhydroxyalkanoate biosynthesis-related DNA fragment isolated from *Alcaligenes latus*. The DNA fragment comprises genes that encode for polyhydroxyalkanoate synthase, β-ketothiolase, and acetoacetyl-CoA reductase.

12 Claims, 10 Drawing Sheets

FIG. 3A (SEQ ID NO: 1, Nucleotides 1-1680)

```
         10         20         30         40         50         60
GGATCCTGCT GCGCTCGGAC AAAAGCATGG GCCGAGTTTA GCGCGCGCCC TCGGACGCCC
         70         80         90        ·100        110        120
CCGGCAGCGT GCAGGGTTCA CGCCATGTTC AAAAGCGCTG TGAGGCAGGT ATGCTGCACT
        130        140        150
GCGTCAATCC CGCAGTTCCG CAGTCATCCC AGAA
        160        170        180        190        200        210
ATGCAG CTGTACAACT ACTTTCGCTC CTCGGCGTCC TACCGCGTCC GCATCGCACT GGCC
        220        230        240        250        260        270
CTGAAG GGTCTGGCCT ACGAATACAA GCCGGTGCAC CTGCAGAAGA AGGAGCAGTT CGCG
        280        290        300        310        320        330
GAGTCG TATGCGGCCG TGTCGGCCTC GCGCCTGGTG CCGCTGCTGC GCGACGGCGA CGCG
        340        350        360        370        380        390
TCGCTG ACGCAGTCGA TGGCCATCAT CGAGTACCTG GACGAGACCC ATCCGCAGCC GCCG
        400        410        420        430        440        450
CTGCTG CCCTCGGACC CGCTGGGCCG CGCCCGCGTG CGTGCGCTGG CGCAGGACAT CGCC
        460        470        480        490        500        510
TGCGAG ATCCACCCGC TCAACAACCT GCGCGTGCTG CGCTACCTGG CGCACGACCT CAAG
        520        530        540        550        560        570
GTCGGC GAGGACGACA AGAACCGCTG GTACCGCCAC TGGGTCGAGA CCGGCCTGGA GGTG
        580        590        600        610        620        630
GTGGAG CGCCAGCTGG CGGATCACCC GTCCACCGGC CGCTTCTGCC ATGGCGACAC GCCC
        640        650        660        670        680        690
GGCCTG GCCGATTGCG TGCTGGTGCC GCAGATCTTC AACGCCCAGC GTTTCAACTG CCGG
        700        710        720        730        740        750
CTGGAG CACGTGCCCA CCGTGATGCG CGTGTACGAG GCCTGCATGC AGCTCGACGC CTTC
        760        770        780        790
GACAAG ACGCAGCCCT CCGCCTGTCC CGATGCCGAG
        800        810        820        830        840
TAAGGCTCTG CAGGGCGTGC TGAGGCCCGA GTGGCCGGCA CCGGCCGGCG
        850        860        870        880        890        900
TGGGCGCATT CATGAGCACG CGCGAGGGCG GCGTCAGCGC CGCGCCCTGG GACGGCGCCA
        910        920        930        940        950        960
ACCTGGGCGA CGCCGTGGGC GACAGCCCGC AGGCTGTGGA CACCAACCGC GCCCGATTCG
        970        980        990       1000       1010       1020
CCGCCGCCGC CGAGGGCGGC ACGCCGGTGT GGCTGCGCCA GGTCCACGGC ACGCGGGTGC
       1030       1040       1050       1060       1070       1080
TGCGATTGCG CGCCGGCGAG GCCTTGCCGG CGCAGCCGCC CGAGGCCGAT GCCGTGGTCA
       1090       1100       1110       1120       1130       1140
CCGCCGACCC CGGCCTGGTG TGCGTGGTGC AGGTGGCGGA CTGCCTGCCC GTGTTCTTCG
       1150       1160       1170       1180       1190       1200
CAGCGTCCAA CGGCCGTGCC GTCGGCGCTG CGCATGCGGG CTGGCGCGGC CTGGCCGGTG
       1210       1220       1230       1240       1250       1260
GCGTGCTCGA AAACACGCTG GCCGAGGTGT GCGCGCTGGC GCGCTGCGAG CCCTCCGATG
       1270       1280       1290       1300       1310       1320
TGCTGGCCTG GATGGGGCCC TGCATCGGGC GGAGAGTTT CGAGGTGGGG CGCGACGTGC
       1330       1340       1350       1360       1370       1380
TGGAGGGTTT CGGCGTGGAT CCGGACGGTC CGGCCGACCC GGCCTTCGCC TGGCGTCCGC
       1390       1400       1410       1420       1430       1440
GTGCCGACGG CAGCGCGCGC TGGCTGGCGG ACCTGCCGGG GCTGGCGCGG CGCCGGCTCG
       1450       1460       1470       1480       1490       1500
AATTGGCAGG TCTGCGTCAG ATCAGTGGCG GACAGTGGTG CACGGTGCAG GATCGTTCAC
       1510       1520       1530       1540       1550       1560
GGTTCTTCTC GTTCCGGCGG GACCGGGTCA CGGGGCGGCA GGCTGCCGCC GTCTGGCTGC
       1570       1580       1590       1600       1610       1620
GCGGATGAAG CGGTGTCCTC GGCGCGCTTG CGCGCCCGTC GCCGCGCCGG CGTCCCCAGG
       1630       1640       1650       1660       1670       1680
AAGTACAGGA CGATGGACAA GGGCAGTACG CCATACAGCA GCAGCGTGAA CACCGCGCCG
```

FIG. 3B
(SEQ ID NO: 1, Nucleotides 1681-2574)

```
          1690       1700       1710       1720       1730       1740
     AGCAAGGTGC CGTTGGGCGC CATGGCTTCG GCCACGGCCA TCATCAGCAC CACGTACAGC
                    -35                              -10
          1750       1760       1770       1780       1790       1800
     CATGCCAGAG CAACCAAGTA CATAGCAAAA ACCCGCAATT ACGCAGAATG ACGTATTTCG
          1810       1820       1830       1840       1850       1860
     TACAATGAAA ACTGTTGTCA TGATGCGGTA AGACACGAAG CCTACAACGC GATCCAGCAA
          1870       1880       1890       1900       1910       1920
     CGGTTTTCGT GAAAAAGTCC TCAGGAGACG AGCGTGACAC TGCATCCCAT TCCCGCACTG
          1930       1940       1950       1960       1970       1980
     CAACAGCTTG GCGACAACGC CACGGCGCTG AGTGCCGCCA TCTCGGAAGC GCTGCGCGCG
```

```
        1989      1998      2007      2016      2025      2034
     ATG TCG GGC CTG AAC CTG CCG ATG CAG GCC ATG ACC AAG CTG CAG GGC GAG TAC
      M   S   G   L   N   L   P   M   Q   A   M   T   K   L   Q   G   E   Y
     phaC_{Au} → (Residues 1-198 of SEQ ID NO: 5)
        2043      2052      2061      2070      2079      2088
     CTC AAC GAG GCG ACG GCG CTG TGG AAC CAG ACG CTG GGC CGC CTG CAG CCC GAC
      L   N   E   A   T   A   L   W   N   Q   T   L   G   R   L   Q   P   D
        2097      2106      2115      2124      2133      2142
     GGC AGC GCC CAA CCG GCC AAG CTG GGC GAC CGG CGC TTC TCG GCC GAG GAC TGG
      G   S   A   Q   P   A   K   L   G   D   R   R   F   S   A   E   D   W
        2151      2160      2169      2178      2187      2196
     GCC AAG AAC CCC GCC GCG GCC TAC CTG GCG CAG GTC TAC CTG CTC AAT GCC CGC
      A   K   N   P   A   A   A   Y   L   A   Q   V   Y   L   L   N   A   R
        2205      2214      2223      2232      2241      2250
     ACG CTG ATG CAG ATG GCC GAG TCC ATC GAG GGC GAC GCC AAG GCC AAG GCG CGC
      T   L   M   Q   M   A   E   S   I   E   G   D   A   K   A   K   A   R
        2259      2268      2277      2286      2295      2304
     GTG CGC TTC GCC GTG CAG CAG TGG ATC GAC GCC GCG GCG CCG AGC AAC TTC CTG
      V   R   F   A   V   Q   Q   W   I   D   A   A   A   P   S   N   F   L
        2313      2322      2331      2340      2349      2358
     GCG CTC AAT CCC GAG GCG CAG CGC AAG GCG CTG GAG ACC AAG GGG GAG AGC ATC
      A   L   N   P   E   A   Q   R   K   A   L   E   T   K   G   E   S   I
        2367      2376      2385       2394      2403      2412
     AGC CAG GGC CTG CAG CAG CTG TGG CAT GAC ATC CAG CAG GGC CAC GTG TCG CAG
      S   Q   G   L   Q   Q   L   W   H   D   I   Q   Q   G   H   V   S   Q
        2421      2430      2439      2448      2457      2466
     ACG GAC GAG AGC GTG TTC GAG GTG GGC AAG AAC GTC GCC ACC ACC GAG GGC GCG
      T   D   E   S   V   F   E   V   G   K   N   V   A   T   T   E   G   A
        2475      2484      2493      2502      2511      2520
     GTC GTG TAC GAG AAC GAC CTG TTC CAG CTC ATC GAG TAC AAG CCG CTG ACG CCC
      V   V   Y   E   N   D   L   F   Q   L   I   E   Y   K   P   L   T   P
        2529      2538      2547      2556      2565      2574
     AAG GTG CAC GAG AAG CCG ATG CTG TTC GTG CCG CCG TGC ATC AAC AAC TAC TAC
      K   V   H   E   K   P   M   L   F   V   P   P   C   I   N   K   Y   Y
```

FIG. 3C
(SEQ ID NO: 1, Nucleotides 2575-3330)

```
     2583          2592          2601          2610          2619          2628
ATC CTG GAC CTG CAG CCG GAC AAC AGC CTC ATC CGC TAC ACC GTC GCC CAG GGC
 I   L   D   L   Q   P   D   N   S   L   I   R   Y   T   V   A   Q   G
```

--> (SEQ ID NO: 5 continued, residues 199 through 432)

```
     2637          2646          2655          2664          2673          2682
CAC CGG GTG TTC GTG GTG AGC TGG CGC AAC CCC GAC GCC TCC GTC GCC GGC AAG
 H   R   V   F   V   V   S   W   R   N   P   D   A   S   V   A   G   K 2691          2700          2709          2718          2727          2736
ACC TGG GAC GAC TAC GTG GAG CAG GGC GTG ATC CGC GCC ATC CGC GTC ATG CAG
 T   W   D   D   Y   V   E   Q   G   V   I   R   A   I   R   V   M   Q 2745          2754          2763          2772          2781          2790
CAG ATC ACG GGG CAC GAG AAG GTC AAC GCG CTG GGC TTC TGC GTC GGC GGC ACC
 Q   I   T   G   H   E   K   V   N   A   L   G   F   C   V   G   G   T 2799          2808          2817          2826          2835          2844
ATC CTG AGC ACG GCG CTG GCG GTG CTG GCC GCG CGC GGC GAG CAG CCC GCG GCG
 I   L   S   T   A   L   A   V   L   A   A   R   G   E   Q   P   A   A 2853          2862          2871          2880          2889          2898
AGC CTG ACG CTG CTG ACC ACG CTG CTG GAC TTC AGC AAC ACC GGC GTG CTG GAC
 S   L   T   L   L   T   T   L   L   D   F   S   N   T   G   V   L   D 2907          2916          2925          2934          2943          2952
CTG TTC ATC GAC GAG GCC GGC GTG CGC CTG CGC GAG ATG ACC ATC GGC GAG AAG
 L   F   I   D   E   A   G   V   R   L   R   E   M   T   I   G   E   K 2961          2970          2979          2988          2997          3006
GCG CCC AAC GGC CCG GGC CTG CTC AAC GGC AAG GAG CTG GCC ACC ACC TTC AGC
 A   P   N   G   P   G   L   L   N   G   K   E   L   A   T   T   F   S 3015          3024          3033          3042          3051          3060
TTC CTG CGC CCG AAC GAC CTG GTC TGG AAC TAC GTG GTG GGC AAC TAC CTC AAG
 F   L   R   P   N   D   L   V   W   N   Y   V   V   G   N   Y   L   K 3069          3078          3087          3096          3105          3114
GGC GAG GCG CCG CCG CCC TTC GAC CTG CTG TAC TGG AAC TCC GAC AGC ACC AAC
 G   E   A   P   P   P   F   D   L   L   Y   W   N   S   D   S   T   N 3123          3132          3141          3150          3159          3168
ATG GCC GGG CCC ATG TTC TGC TGG TAC CTG CGC AAC ACC TAC CTG GAG AAC AAG
 M   A   G   P   M   F   C   W   Y   L   R   N   T   Y   L   E   N   K 3177          3186          3195          3204          3213          3222
TTG CGC GTT CCC GGT GCC CTG ACC ATC TGC GGC GAG AAG GTG GAC CTC TCG CGC
 L   R   V   P   G   A   L   T   I   C   G   E   K   V   D   L   S   R 3231          3240          3249          3258          3267          3276
ATC GAG GCG CCG GTG TAC TTC TAC GGT TCG CGC GAG GAC CAC ATC GTG CCC TGG
 I   E   A   P   V   Y   F   Y   G   S   R   E   D   H   I   V   P   W 3285          3294          3303          3312          3321          3330
GAA TCG GCC TAC GCC GGC ACG CAG ATG CTG AGC GGC CCC AAG CGC TAT GTC CTG
 E   S   A   Y   A   G   T   Q   M   L   S   G   P   K   R   Y   V   L
```

FIG. 3D (SEQ ID NO: 1, Nucleotides 3331-4076)

```
        3339        3348        3357        3366        3375        3384
GGT GCG TCT GGC CAC ATC GCC GGC GTG ATC AAC CCC CCG CAG AAG AAG AAG CGC
 G   A   S   G   H   I   A   G   V   I   N   P   P   Q   K   K   K   R
--> (SEQ ID NO: 5 continued, residues 433 through 536)

3393        3402        3411        3420        3429        3438
AGC TAC TGG ACC AAC GAG CAG CTC GAC GGC GAC TTC AAC CAG TGG CTG GAA GGC
 S   Y   W   T   N   E   Q   L   D   G   D   F   N   Q   W   L   E   G 3447        3456        3465        3474        3483        3492
TCC ACC GAG CAT CCT GGC AGC TGG TGG ACC GAC TGG AGC GAC TGG CTC AAG CAG
 S   T   E   H   P   G   S   W   W   T   D   W   S   D   W   L   K   Q 3501        3510        3519        3528        3537        3546
CAC GCG GGC AAG GAA ATC GCC GCA CCC AAG ACT CCC GGC AAC AAG ACC CAC AAG
 H   A   G   K   E   I   A   A   P   K   T   P   G   N   K   T   H   K 3555        3564        3573        3582
CCC ATC GAG CCC GCC CCC GGG CGT TAC GTG AAG CAG AAG GCC
 P   I   E   P   A   P   G   R   Y   V   K   Q   K   A 3600        3610        3620        3630        3640
TG AGCCGCGGCC CCTGAGCCTT CTTTAACCCG ACCTTGACAA ACGAGGAGAT AAGC 3653        3662        3671        3680        3689        3698
ATG ACC GAC ATC GTC ATC GTC GCC GCA GCC CGC ACC GCC GTG GGC AAG TTC GGC
 M   T   D   I   V   I   V   A   A   A   R   T   A   V   G   K   F   G
phaA_AI --> (SEQ ID NO: 6, residues 1-144)

3707        3716        3725        3734        3743        3752
GGC ACG CTG GCC AAG ACC CCC GCT CCG GAG CTG GGC GCC GTG GTC ATC AAG GCC
 G   T   L   A   K   T   P   A   P   E   L   G   A   V   V   I   K   A 3761        3770        3779        3788        3797        3806
CTG CTG GAG AAG ACG GGC GTC AAG CCC GAC CAG ATC GGT GAA GTC ATC ATG GGC
 L   L   E   K   T   G   V   K   P   D   Q   I   G   E   V   I   M   G 3815        3824        3833        3842        3851        3860
CAG GTG CTG GCC GCC GGC GCG GGC CAG AAC CCC GCG CGC CAG GCG ATG ATG AAG
 Q   V   L   A   A   G   A   G   Q   N   P   A   R   Q   A   M   M   K 3869        3878        3887        3896        3905        3914
GCG GGC ATC GCC AAG GAA ACG CCG GCG CTG ACC ATC AAC GCC GTG TGC GGC TCC
 A   G   I   A   K   E   T   P   A   L   T   I   N   A   V   C   G   S 3923        3932        3941        3950        3959        3968
GGC CTC AAG GCC GTG ATG CTG GCC GCC CAG GCC ATC GCC TGG GGC GAC AGC GAC
 G   L   K   A   V   M   L   A   A   Q   A   I   A   W   G   D   S   D 3977        3986        3995        4004        4013        4022
ATC GTC ATC GCC GGC GGC CAG GAG AAC ATG AGC GCC AGC CCG CAC GTG CTG ATG
 I   V   I   A   G   G   Q   E   N   M   S   A   S   P   H   V   L   M 4031        4040        4049        4058        4067        4076
GGC AGC CGC GAC GGC CAG CGC ATG GGC GAC TGG AAG ATG GTC GAC ACC ATG ATC
 G   S   R   D   G   Q   R   M   G   D   W   K   M   V   D   T   M   I
```

FIG. 3E (SEQ ID NO: 1, Nucleotides 4077-3820)

```
         4085        4094        4103        4112        4121        4130
AAC GAC GGC CTG TGG GAC GTG TAC AAC AAG TAC CAC ATG GGC ATC ACG GCC GAG
 N   D   G   L   W   D   V   Y   N   K   Y   H   M   G   I   T   A   E
```
-- > (SEQ ID NO: 6 continued, residues 145 through 392)
```
         4139        4148        4157        4166        4175        4184
AAC GTC GCC AAG GAA CAC GAC ATC AGC CGC GAC CAG CAG GAC GCC CTG GCC CTG
 N   V   A   K   E   H   D   I   S   R   D   Q   Q   D   A   L   A   L 4193        4202        4211        4220        4229        4238
GCC AGC CAG CAG AAG GCC ACC GCC GCG CAG GAA GCC GGC CGC TTC AAG GAC GAG
 A   S   Q   Q   K   A   T   A   A   Q   E   A   G   R   F   K   D   E 4247        4256        4265        4274        4283        4292
ATC GTT CCG GTC TCG ATC CCG CAG CGC AAG GGC GAC CCG GTG CTG TTC GAC ACC
 I   V   P   V   S   I   P   Q   R   K   G   D   P   V   L   F   D   T 4301        4310        4319        4328        4337        4346
GAC GAG TTC ATC AAC AAG AAG ACC ACC GCC GAA GCG CTG GCG GGC CTG CGC CCG
 D   E   F   I   N   K   K   T   T   A   E   A   L   A   G   L   R   P 4355        4364        4373        4382        4391        4400
GCC TTC GAC AAG GCC GGC AGC GTG ACC GCG GGC AAC GCC TCG GGC ATC AAC GAC
 A   F   D   K   A   G   S   V   T   A   G   N   A   S   G   I   N   D 4409        4418        4427        4436        4445        4454
GGC GCC GCT GCG GTG ATG GTG ATG TCC GCC GCC AAG GCG AAG GAG CTG GGC CTG
 G   A   A   A   V   M   V   M   S   A   A   K   A   K   E   L   G   L 4463        4472        4481        4490        4499        4508
ACG CCC ATG GCG CGC ATC AAG AGC TTC GGC ACC AGC GGC CTG GAT CCG GCC ACC
 T   P   M   A   R   I   K   S   F   G   T   S   G   L   D   P   A   T 4517        4526        4535        4544        4553        4562
ATG GGC ATG GGC CCG GTG CCG GCC TCG CGC AAG GCG CTG GAG CGC GCC GGC TGG
 M   G   M   G   P   V   P   A   S   R   K   A   L   E   R   A   G   W 4571        4580        4589        4598        4607        4616
CAG GTC GGT GAC GTG GAC CTG TTC GAG CTC AAC GAA GCC TTC GCC GCC CAG GCC
 Q   V   G   D   V   D   L   F   E   L   N   E   A   F   A   A   Q   A 4625        4634        4643        4652        4661        4670
TGC GCG GTG AAC AAG GAG CTG GGC GTG GAT CCG GCC AAG GTC AAC GTC AAC GGC
 C   A   V   N   K   E   L   G   V   D   P   A   K   V   N   V   N   G 4679        4688        4697        4706        4715        4724
GGT GCC ATC GCC ATC GGC CAC CCC ATC GGC GCC TCC GGC TGC CGC GTG CTG GTG
 G   A   I   A   I   G   H   P   I   G   A   S   G   C   R   V   L   V 4733        4742        4751        4760        4769        4778
ACG CTG CTG CAC GAG ATG CAG CGC CGG GAC GCC AAG AAG GGC CTG GCC GCG CTG
 T   L   L   H   E   M   Q   R   R   D   A   K   K   G   L   A   A   L 4787        4796        4805        4814
TGC ATC GGC GGC GGC ATG GGC GTG TCG CTG ACC GTC GAG CGC
 C   I   G   G   G   M   G   V   S   L   T   V   E   R
```

FIG. 3F
(SEQ ID NO: 1, Nucleotides 4821-5640)

```
            4830       4840       4850       4860       4870       4880
        TGATCAGAAG AACCGGGCGG CCCCGCGCCG CCCGCCCGGC GTTCCACGCG GGTGCGCCGG
            4890       4900       4910       4920       4930
        GATACCAGAC GAACCAAACC ACCAAGGGCT TCGAGACGGC CCGAAGAAGG AGAGACAG
```

```
     4947       4956       4965       4974       4983       4992
ATG GCA CAG AAA CTG GCT TAC GTG ACC GGC GGC ATG GGC GGC ATC GGC ACC TCG
 M   A   Q   K   L   A   Y   V   T   G   G   M   G   G   I   G   T   S
```
phaB$_{A1}$ → (SEQ ID NO: 7, residues 1-234)

```
     5001       5010       5019       5028       5037       5046
ATG TGC CAG CGC CTG CAC AAG GAC GGC TTC AAG GTG ATC GCC GGC TGC GGT CCG
 M   C   Q   R   L   H   K   D   G   F   K   V   I   A   G   C   G   P 5055       5064       5073       5082       5091       5100
AGC CGC GAC CAC CAG AAG TGG ATC GAT GAA CAG GCC GCG CTG GGC TAT ACC TTC
 S   R   D   H   Q   K   W   I   D   E   Q   A   A   L   G   Y   T   F 5109       5118       5127       5136       5145       5154
TAC GCC TCC GTG GGC AAC GTG GCC GAC TGG GAC TCC ACC GTG GCC GCC TTC GAG
 Y   A   S   V   G   N   V   A   D   W   D   S   T   V   A   A   F   E 5163       5172       5181       5190       5199       5208
AAG GTC AAG GCC GAG CAC GGC ACC GTG GAC GTG CTG GTG AAC AAC GCC GGC ATC
 K   V   K   A   E   H   G   T   V   D   V   L   V   N   N   A   G   I 5217       5226       5235       5244       5253       5262
ACG CGT GAC GGG CAG TTC CGC AAG ATG AGC AAG GCC GAT TGG CAG GCC GTG ATG
 T   R   D   G   Q   F   R   K   M   S   K   A   D   W   Q   A   V   M 5271       5280       5289       5298       5307       5316
TCG ACC AAC CTC GAC AGC ATG TTC AAC GTC ACC AAG CAG GTG ATC GAG GGC ATG
 S   T   N   L   D   S   M   F   N   V   T   K   Q   V   I   E   G   M 5325       5334       5343       5352       5361       5370
CTG GAC AAG GGC TGG GGC CGG ATC ATC AAC ATC TCC TCG GTC AAC GGC GAG AAG
 L   D   K   G   W   G   R   I   I   N   I   S   S   V   N   G   E   K 5379       5388       5397       5406       5415       5424
GGC CAG TTC GGC CAG ACC AAC TAC TCC GCC GCC AAG GCC GGC ATG CAC GGC TTC
 G   Q   F   G   Q   T   N   Y   S   A   A   K   A   G   M   H   G   F 5433       5442       5451       5460       5469       5478
TCG ATG GCG CTG GCG CAG GAA GTG GCG GCC AAG GGC GTG ACG GTG AAC ACC GTG
 S   M   A   L   A   Q   E   V   A   A   K   G   V   T   V   N   T   V 5487       5496       5505       5514       5523       5532
AGC CCG GGC TAC ATC GCC ACG GAC ATG GTC AAG GCC ATC CGC CAG GAC GTG CTG
 S   P   G   Y   I   A   T   D   M   V   K   A   I   R   Q   D   V   L 5541       5550       5559       5568       5577       5586
GAC AAG ATC ATC GCC ACC ATT CCC ATC CGT CGC CTG GGT ACG CCG GAG GAG ATC
 D   K   I   I   A   T   I   P   I   R   R   L   G   T   P   E   E   I 5595       5604       5613       5622       5631       5640
GCC TCC ATC GTC GCC TGG CTG GCC GGC GAG GAG TCG GGC TTC ACC ACC GGT GCC
 A   S   I   V   A   W   L   A   G   E   E   S   G   F   T   T   G   A
```

FIG. 3G
(SEQ ID NO: 1, Nucleotides 5640-6436)

```
         5649           5658           5667
      GAC TTC AGC TGC AAC GGC GGC CTG CAC ATG GGC
       D   F   S   C   N   G   G   L   H   M   G
    -- > (SEQ ID NO: 7 continued, residues 235 through 245)

5680       5690       5700       5710       5720       5730
     TGAGGCC    CGCGGCTCCA TGCCCACCTG CGTGGGCATG GACGGGCCGA AGGACCCGAG
                           ————————→  ←————————
       5740       5750       5760       5770       5780       5790
    CTCTGCGAGG GTGCGGCCTG CAAGGCTGAG GCCTGCTGCG CCGCGTGCCC GCGAGGGCAC
       5800       5810       5820       5830       5840       5850
    GTGCCGAAGC ACCAAAAGGC CGCGCATTGC GCGGCCTTTT CCTTTCTGGA TCGGTGCGGA
       5860       5870       5880       5890       5900       5910
    CGGGTGCCGC GTCAGGCAGG GCAGGGCCCC CGGGCCTTCA CTCCACCATG CCCGACATGA
       5920       5930       5940       5950       5960       5970
    AGTACTTGAT CAGCCCCTTG GCCGCGAAGC CCAGCATGCC GAAGCCCAGC GCCAGGAACA
       5980       5990       6000       6010       6020       6030
    GCACGAAGGT GCCGAACTTG CCGGCCTTCG ACTCGCGCGC GAGCTGAAAG ATGATGAATG
       6040       6050       6060       6070       6080       6090
    CCATGTAGAG CATGAAGGCC GTGACGCCGA CGGTCAGGCC CAGCTGGGCA ATGTTTTCCT
       6100       6110       6120       6130       6140       6150
    CGTTGATTTC GAACATCGTT TGTTGTCTCA GGCTGCTGCA CGCGGCTGAC GTGCTCGCCG
       6160       6170       6180       6190       6200       6210
    CGCGGCCGGG CCCCAACTGC CCGCAGCGGT TCTCGATCAG GTTCTCAAGG CATCTCGTGC
       6220       6230       6240       6250       6260       6270
    CACTGGGAGG TGTCCACCAG GTCGCGGTAG GCGTGCCAGC TCGAATGCGC CAGCCACGGC
       6280       6290       6300       6310       6320       6330
    ACTACCACGA TCAGGCCCAG CAGCAGCGTG GCCATGCCCA GCAGCGTCA GCGCCATGATC
       6340       6350       6360       6370       6380       6390
    AGCGCCGCCC ACAGCGCCAG CGGCAGTGGG TGCTGCATCA CCACGCGCCA GCTCGTGAGC
       6400       6410       6420       6430
    ACCGCCACCA GCACGCCCAC GTGGCGGTCC AGCAGCATCG GGATCC
```

METHODS OF MAKING POLYHYDROXYALKANOATE USING BIOSYNTHESIS GENES FROM ALCALIGENES LATUS

BACKGROUND OF THE INVENTION

1. Field of the Invention

The present invention relates to polyhydroxyalkanoate (hereinafter referred to as "PHA") biosynthesis-related genes for PHA synthase, β-ketothiolase and acetoacetyl-CoA reductase, derived from *Alcaligenes latus*, their amino acid sequences, a recombinant plasmid carrying these genes, and a method for mass producing PHA using these genes.

2. Description of the Prior Art

Petroleum synthetic plastics are so durable that they are not degraded in usual conditions at all. Because the production amount of the petroleum synthetic plastics increases each year, the environmental pollution ascribed to petroleum synthetic plastics wastes are now a big social problem. To solve the problem of non-degradable plastics, active research and development efforts have been and continued to be directed to biodegradable polymers all over the world.

Biodegradable polymers are the high molecular weight materials that are completely degraded under natural conditions after a period of time. Many biodegradable polymers have been developed. Of them, PHA, a natural polyester which is synthesized and accumulated by microorganisms, is of particular interest because it is superior in biodegradability as well as shows physical properties similar to those of the synthetic plastics in current use (Anderson A. J. and Dawes, E. A., *Microbiol. Rev.*, 1990, 54, 450–472; Lee, S. Y., *Biotechnol. Bioeng.*, 49:1–14,1996; Lee, S. Y., *Trends Biotechnol.*, 14:431 –438, 1996).

In detail, PHA is an organic reserve material, which can provide an intracellular store of carbon or energy, usually found in Pseudomonas, Alcaligenes, Azotobacter, and Bacillus spp.,etc. It is detectable as granular cytoplasmic inclusions. As a general rule, the cellular content of the reserve material is relatively low in actively growing cells: They accumulate massively when cells are limited in nitrogen, phosphorous, sulfur, oxygen, etc., but still have carbon and energy available. This reserve material was first found in *Bacillus megaterium* by Lemoigne in 1925 (Lemoigne, M., *Bull. Soc. Chem. Biol.*, 8:770–782, 1926). Since then, its chemical and physical properties have been extensively researched. Poly(3-hydroxybutyrate) is the most widely, and first known PHA.

According to the number of carbon atoms and the substituents in hydroxyalkanoate, many PHAs were reported. In general, PHAs are divided into two classes; short-chain-length PHAs(SCL PHAs) and medium-chain-length PHAs (MCL PHAs)

SCL PHAs include poly-β-hydroxypropionic acid, poly-β-hydroxybutyric acid, and poly-β-hydroxyvaleric acid, which are produced by *Alcaligenes eutrophus, Azotobacter vinelandii, methylotrophs*, etc. SCL PHAs are widely used due to their similar properties to polypropylene, a kind of chemically synthesized plastics.

MCL PHAs, composed of 3 to 9 more carbon atoms than SCL PHAs, are produced by Pseudomonas spp., by using alkane, 1-alkene, $C_6$~$C_{12}$ alkanoic acids as a carbon.

Since early the 1960s, it was recognized that PHA could work like thermoplastic polymers. Thereafter, attracting a great attention, many types of PHA copolymers were synthesized, which are superior in mechanical properties as well as in biodegradability. By virtue of these advantages and owing to the environmental pollution aggravated by petroleum synthetic polymer wastes, PHA is now actively researched and developed as an alternative for plastics over the world. In addition, biocompatibility and bioabsorptivity allow PHA to be used in a variety of fields, as materials for agriculture, medicinal care, drug transfer system, and package, and as precursors for fine chemical products (Holmes, P. A. in Developments in crystalline polymers. 1–65, 1988).

Taking advantage of various bacteria, molecular biological research has revealed that there are four different biosynthetic pathway for PHA (Steinbuchel, A. in Biomaterials: novel materials from biological sources, 215–262, 1991). For example, for *Alcaligenes eutrophus*, the most widely known bacteria, β-ketothiolase, acetoacetyl-CoA reductase and polyhydroxyalkanoate synthase (PHA synthase) are known to be involved in the biosynthesis of PHA (People, O. P. and Shinskey, A. J., *J. Biol Chem.*, 264: 15298–15303, 1989; Schubert, P., Steinbuchel, A. and Schlegel, H. G., *J. Bacteriol.*, 170:5837–5847, 1988; Slater, S. C., Voige, W. H. and Dennis, D. E., *J. Bacteriol.*, 170:4431–4436, 1988).

A concrete biosynthetic pathway of PHA in *Alcaligenes eutrophus*, gram negative bacteria, is as follows. Between two molecules of acetyl-CoA, a carbon-carbon bond forms in the presence of β-ketothiolase, the product of gene phbA , according to a biological Claisen condensation. The acetoacetyl-CoA thus formed is converted into D(-)-β-hydroxybutyryl-CoA by the stereoselective reduction of NADPH-dependent acetoacetyl-CoA reductase, the product of gene phbB. Finally, D(-)-β-hydroxybutyryl-CoA is polymerized via ester bond by PHA synthase, the product of gene phbC.

In order to clone the genes which pertain to the biosynthesis of PHA in other bacteria than *Alcaligenes eutrophus*, much effort has been made. That is, the comprehension of the biosynthesis of PHA in bacteria makes it possible efficient production of PHA, versatility of substrates, synthesis of new PHA, and development of biopolymers similar to PHA. Further, recombinant strains which are obtained by utilizing the PHA biosynthesis-related genes can synthesize various PHAs at high efficiencies, resulting in a scientific and industrial significance (Lee, S. Y., *Trends Biotechnol.*, 14:431–438, 1996).

Strain *Alcaligenes latus* is reported to be so superior in the production of PHA that it accumulates PHA in cells at a proportion of around 90%. Also, *Alcaligenes latus* as the advantage in that it grows fast and uses inexpensive substrates as carbon sources (Wang, F. and Lee, S. Y., *Appl. Environ. Microbiol.*, 63:3703–3706, 1997). Unlike *Alcaligenes eutrophus, Alcaligenes latus* accumulates PHAs while they are growing. Thus, *Alcaligenes latus* can mass-produce PHA by one-step culture although the amount is low relative to that upon *Alcaligenes eutrophus*.

The use of *Alcaligenes latus* to produce PHA began in earnest in the mid-1980s by Chemie Linz AG, Austria. Biotechnologishe forchungesellschaft mbH, Austria, developed a process in which a one-step culture of strain btF-96, a mutant strain of *Alcaligenes latus.*, produces PHA, asserting that one ton of PHA is obtained from a 15 $m^3$ ferinentor per week (Hrabak, O., FEMS *Microbial. Rev.*, 103:251–256, 1992). *Alcaligenes latus* also produces poly(3-hydroxybutyrate/3-hydroxypropionate) as well as poly(3-hydroxybutyrate/4-hydroxypropionate) in a medium containing disaccharides as carbon source by addition of 3-hydroxypropionate and γ-butyrolactone (Hiramitsu, M., Koyama, N., and Doi, Y., *Biotechnol. Leit.*, 15:461–464, 1993).

PHA can be produced by chemical process as well as biological process. However, Commercially favorable production scale of PHA is possible only by biological process. Since the production cost of PHA is much higher than those of other commercially available synthetic polymers, new technologies are required to reduce the production cost of PHA. Particularly, recombinant DNA technology gives a great contribution to the development and modification of novel strains, showing the production of novel polymers, utility of low-priced substrate, high efficiency of production, and facility in separation and purification. In order to develop such recombinant strains, first of all, it is necessary to understand the enzymes involved in the biosynthetic pathway for PHA.

In order to mass-produce biodegradable, natural PHA and its copolymers, the inventors have cloned genes for polyhydroxyalkanoate synthase, β-ketothiolase, and acetoacetyl-CoA reductase, and determined amino acid sequences and gene sequences. They have made expression vectors carrying the above genes and transformants, whereby polyhydroxyalkanoate can be produced and accumulated.

BRIEF DESCRIPTION OF THE DRAWINGS

FIGS. 3A through 3G illustrate the nucleotide sequence of a DNA fragment 6.4 kb in size (SEQ ID NO: 1), which encodes three PHA biosynthesis-related genes derived from *Alcaligenes latus*. Each of FIGS. 3A–3G illustrates a sequential block of SEQ ID NO:1, with open reading frames ("ORFs") for the three expressed proteins indicated by the corresponding protein expression products of the 6.4 kb DNA fragment of SEQ ID NO: 1.

FIG. 3A shows the DNA molecule of SEQ ID NO: 1, from nucleotide 1 through nucleotide 1680.

FIG. 3B shows the DNA molecule of SEQ ID NO: 1, from nucleotide 1681through nucleotide 2574. Starting at nucleotide 1981 is the ATG start of the ORF encoding PHA synthase, from residues 1 through 198 of SEQ ID NO: 5.

FIG. 3C shows the DNA molecule of SEQ ID NO: 1, from nucleotide 2575 through nucleotide 3330, and continues the PHA ORF from residues 199 through 450 of SEQ ID NO: 5.

FIG. 3D shows the DNA molecule of SEQ ID NO: 1, from nucleotide 3331 through nucleotide 4076, and continues the PHA ORF from residues 451 through terminal residue 536 of SEQ ID NO: 5. Starting at nucleotide 3645 is the ATG start of the ORF encoding beta-ketothiolase, from residue 1 through residue 144 of SEQ ID NO: 6.

FIG. 3E shows the DNA molecule of SEQ ID NO: 1, from nucleotide 4077 through nucleotide 3820. The ORF of beta-ketothiolase is continued, from residues 145 through terminal residue 392 of SEQ ID NO: 6.

FIG. 3F shows the DNA molecule of SEQ ID NO: 1, from nucleotide 4821 through nucleotide 5640. Starting at nucleotide 4939 is the ATG start of the ORF encoding acetoacetyl-CoA reductase, from residue 1 through residue 234 of SEQ ID NO: 7.

FIG. 3G shows the DNA molecule of SEQ ID NO: 1, from nucleotide 5640 through 6436, and continues the acetyl CoA reductaase ORF, from residue 235 through terminal residue245 of SEQ ID NO: 7.

DETAILED DESCRIPTION OF THE INVENTION

The present invention provides polyhydroxyalkanoate biosynthesis-related genes.

The present invention provides an expression vector containing the polyhydroxyalkanoate biosynthesis-related genes and their transformant.

The present invention further provides methods for preparing polyhydroxyalkanoate synthase enzyme. Further still, the invention further provide methods for producing PHAs, including polyhybroxybutyrates, and preferably poly(3-hydroxybutyrate, using vectors and host cells described herein.

In the present invention, genes for the biosynthesis of PHA, are separated from *Alcaligenes latus*, which accumulates PHA while growing, whereby biodegradable, natural and industrially useful PHA and its copolymers can be mass-produced.

Figure 1:
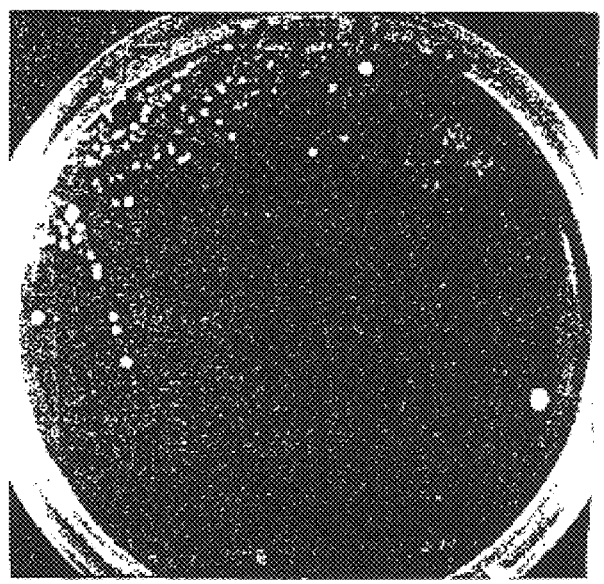
FIG. 1 is a photograph showing opaque colonies of recombinant *E. coli* containing PHA biosynthesis-related genes derived from *Alcaligenes latus*, formed on a solid medium.
Figure 2:
FIG. 2 is a photograph showing that recombinant *E. coli* containing PHA biosynthesis-related genes accumulates PHA in a broth.

In more detail, the total genomic DNA separated from *Alcaligenes latus* is partly digested by restriction enzymes and the resulting DNA fragments are inserted into vector pUC19. *E. coli* is transformed with vector pUC19, followed by the selection of the recombinant vectors with a PHA biosynthesis-related DNA. The bacteria harboring the interest DNA was observed to accumulate PHA on a solid medium and in a liquid medium, as shown in FIGS. 1 and 2, respectively.

Isolation of the recombinant vector from the transformed bacteria capable of producing PHA is the first step in a process of identifying the DNA fragment of interest. Various analytic works show that the DNA fragment of interest is 6.4 kb in size, containing the genes coding for all of the β-ketothiolase, acetoacetyl-CoA reductase and PHA synthase.

Therefore, in accordance with one aspect, the present invention pertains to a PHA biosynthesis-related DNA fragment containing a PHA synthase gene, a β-ketothiolase gene and an acetoacetyl-CoA reductase gene, in due order, which has a size of 1608 bp (corresponding to 536 aa), 1176 bp (392 aa) and 735 bp (245 aa), respectively.

Sequencing analyses reveal that the PHA synthase gene (phbC) has a base sequence of Sequence 2 with a corresponding amino acid sequence of Sequence 5, as suggested in the accompanying Sequence Lists. The β-ketothiolase gene (phbA) has a base sequence of Sequence 3 and the β-ketothiolase expressed therefrom has an amino acid sequence of Sequence 6. The analyses also give that the acetoacetyl-CoA reductase gene (phbB) has a base sequence of Sequence 4 which corresponds to an amino acid sequence of Sequence 7(see, FIG. 3 and Sequence Listing).

Figure 4:
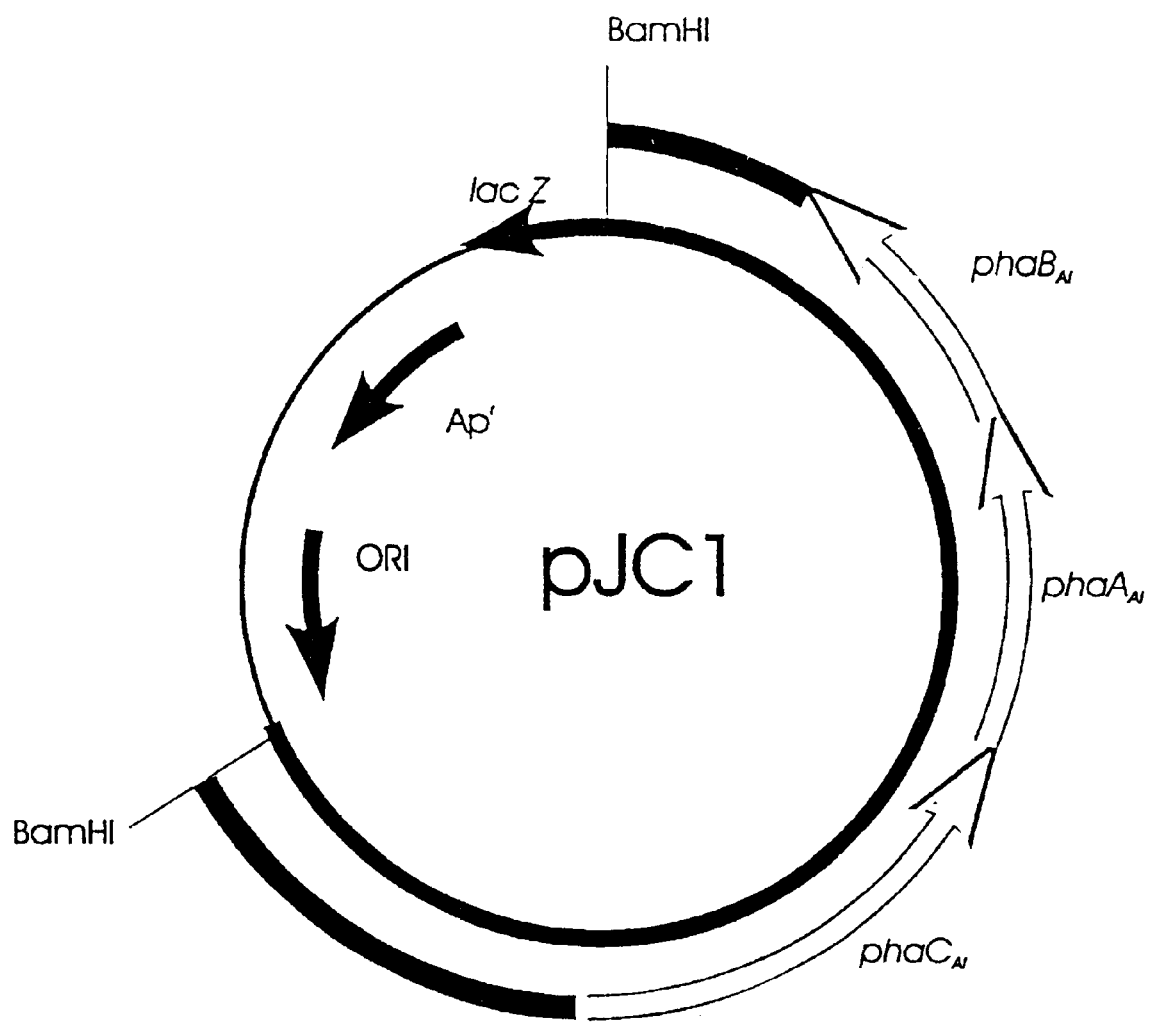
FIG. 4 illustrates the structure of recombinant expression vector pJC1 carrying a PHA biosynthesis-related genes derived from *Alcaligenes latus*.

The recombinant vector anchoring the DNA for biosynthesis of PHA was named pJC1 (see, FIG. 4) and the transformant, *E. coli* XL-1 Blue/pJC1, was deposited in Korean Collection for Type Cultures, Korean Research Institute of Bioscience and Biotechnology on Nov. 5, 1997 and received a Deposition No. KCTC 0398 BP.

In accordance with another aspect, the present invention pertains to the preparation of the PHA biosynthesis-related enzymes by culturing host bacteria which harbor a recombinant expression vector containing the PHA biosynthesis-related genes.

In accordance with a further aspect, the present invention pertains to the production of PHA and its copolymers by use of the above host bacteria which can express the PHA biosynthesis-related genes. To this end, E. coli was transformed by the recombinant expression vector and after selecting, the transformed E. coli was cultured in a liquid medium containing glucose in suitable concentration to produce PHA. Where the E. coli was cultured in this manner, PHA was observed to accumulate until it represent as much as 40% or more of the dry cell weight.

In an alternative aspect of the invention, the total genomic DNA separated from Alcaligenes latus is partly digested by restriction enzyme, followed by selecting the DNA fragment showing a positive signal by use of a PHA gene derived from Alcaligenes eutrophus H16 as a probe. Plasmid vector pAL32 is obtained by inserting the above PHA gene into pSK(+).

Figure 5:
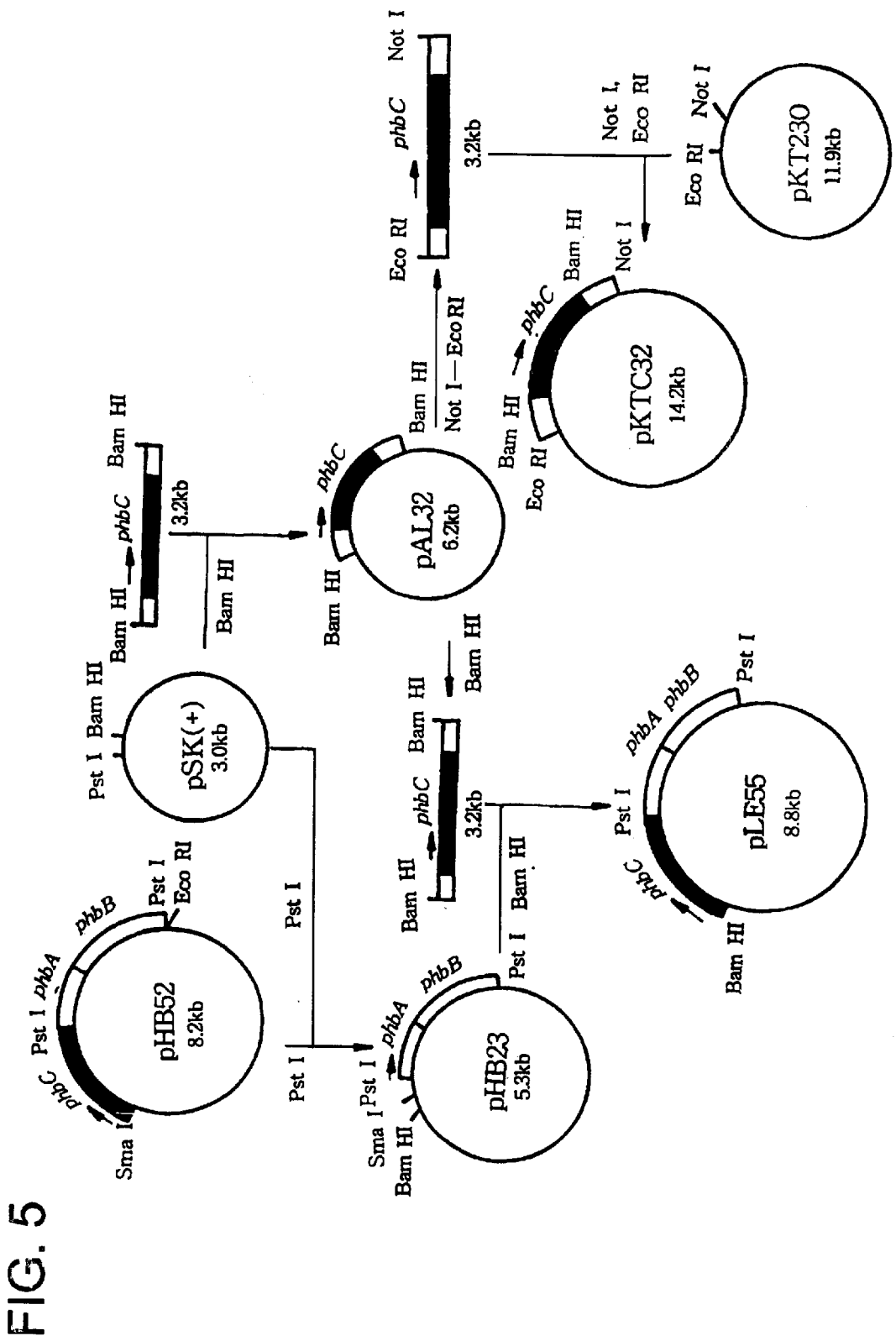
FIG. 5 illustrates the process of preparing the recombinant expression vector carrying a PHA synthase gene derived from *Alcaligenes latus*.

The pAL32 is digested with EcoRI and NotI to obtain the PHA gene. The resulting gene is then inserted into plasmid pK230, that has a broad host range, to obtain the recombinant expression vector pKTC32. This pKTC32 can express the gene in various host cells. This is illustrated by FIG. 5.

The transformant Alcaligenes eutrophus LAR5 was obtained by inserting pKTC32 into Alcaligenes eutrophus DSM541 which is lacking a PHA gene. This vector was deposited under the terms of the Budapest Treaty in the Korean Collection for Type Cultures, Korean Research institute of Bioscience and Biotechnology on Jan. 18, 1999, with the deposit No. KCTC 0568 BP.

When the above transformant Alcaligenes eutrophus DSM541 (phb$^-$)/pKTC32 is cultured, it is observed that PHA synthase is produced in the cell cytoplasm in the form of white particles.

The invention will now be illustrated by the following examples, but not be limited in scope by reason of any of the following examples.

EXAMPLE I

Separation of Genomic DNA from Alcaligenes latus

The strain Alcaligenes latus (Wang, F and Lee. S. Y., Appl. Envirn. Microbiol., 63:3707–3706, 1997) was cultured overnight in 500 ml of an NB medium (8 g/L nutrient broth). The bacteria in an initial stage of exponential growth were harvested by centrifugation and washed twice with saline-EDTA (0.15 M NaCl, 0.1 M EDTA, pH 8.0). The washed bacteria were suspended in 40 ml of 0.1 M saline-Tris-Cl (0.1 M NaCl, 10 mM EDTA, pH 9.0) and 1 ml of lysozyme solution (20 mg/ml) prepared just before use was added to the suspension. This suspension was dropwise added at 37° C. with Tris-SDS buffer (0.4 M NaCl, 1 mM EDTA, 20 mM Tris-Cl, pH 7.5, added with 5% SDS) with slow agitation. When the resulting solution became viscous, 5.5 ml of Proteinase K (10 mg/ml) was added and the total solution was incubated at 37° C. for 2 hours to remove proteins. Next, equal volume of phenol was added to the solution and well mixed for 30 min at room temperature with caution. After the solution was centrifuged at 6,000 rpm for 10 min, the supernatant was transferred to a fresh beaker followed by volume-measurement, and slowly added with two times the volume of cold ethanol to precipitate the genomic DNA which was, then, rolled up with a glass bar. The DNA was dried at room temperature and dissolved in 10 ml of TE buffer (10 mM Tris-HCl, 1 mM EDTA, pH 8.0). Thereafter RNase was added to the above solution until the final concentration became 50 µg/ml and the total solution was incubated at 37° C. for 1 hour. Then the same following process, i.e. mixing with phenol, centrifugation, volume mearsurement, addition of cold ethanol, rolling up, drying, and resuspension in TE buffer, was repeated. The only difference was that the concentration of TE buffer was 2 ml.

EXAMPLE II

Cloning of PHA Biosynthesis-Related Genes

The genomic DNA of Alcaligenes latus, obtained Example I, was partly digested by restriction enzyme Sau3AI. Because restriction enzyme Sau3AI recognizes a specific four-base sequence in double-stranded DNA and cleaves both strands of the duplex at a specific site, various DNA fragments ranging from a small size to a large size can be obtained. These DNA fragments were separated according to size by electrophoresis on a low-melting temperature agarose gel.

To obtain the whole PHA biosynthesis-related gene, only the genes which were as large as or larger than 4 kb in size, were selected and inserted in plasmid pUC19 2.68 kb in size. To this end, first, the plasmid was cut with restriction enzyme BamHI which leaves the same end sequence with restriction enzyme Sau3AI. Then, the genomic DNA fragments at least 4 kb long were ligated with the opened plasmid vector pUC19 by using T4 DNA ligase (New England Biolabs).

The recombinant vector thus obtained was used to transform E. coli XL1-Blue (Stratagene) with the aid of an electroporator. When the recombinant vector pUC19 which contained the whole PHA biosynthesis-related gene at a BamHI cloning site was taken up by E. coli XL1-Blue, white colonies were formed on a solid LB medium (tryptone 10 g/L, yeast extract 5 g/L, NaCl 10 g/L) supplemented with ampicillin, X-gal (5-bromo-4-chloro-3-indolyl-β-D-galactopyranoside) and IPTG (isopropyl-1-thio-β-D-galactopyranoside). On the other hand, where the bacteria contained plasmid vector pUC19 without a DNA insert, blue colonies were formed. Through this procedure, colonies containing plasmid vector pUC19 with a partial genomic DNA insert of Alcaligenes latus, were selected. In order to determine whether these colonies were able to produce PHA, they each were inoculated in a broth capable of accumulating PHA.

As a result, recombinant E. coli were obtained that were able to accumulate PHA. Analysis of the recombinant plasmid vector that was separated from the recombinant E. coli confirmed that Vector pUC19 anchored a partial genomic DNA of Alcaligenes latus, 6.4 kb long, and that this DNA fragment contained the PHA synthesis-related genes. In addition, base sequencing analysis revealed that the 6.4 kb DNA fragment coded for all of the PHA biosynthesis-related enzymes, that is, β-ketothiolase, acetoacetyl-CoA reductase and PHA synthase.

In the present invention, the recombinant expression vector was named pJC1. The transformant which harbored plasmid pJC1 was deposited in Korean Collection for Type Cultures, Korean Research Institute of Bioscience and Biotechnology on Nov. 5, 1997, as Deposit No. KCTC 0398BP.

EXAMPLE III

Structure Analysis of PHA Genes Derived from *A. latus*

The 6.4 kb DNA insert ligated to the plasmid vector pUC19 was analyzed, and the analysis confirmed that the vector contained all of the genes for β-ketothiolase, acetoacetyl-CoA reductase and PHA synthase. These genes were located in the following order (5' to 3'): PHA synthase, β-ketothiolase and acetoacetyl-CoA reductase.

Regarding the sizes of the PHA biosynthesis genes, the PHA synthase gene, β-ketothiolase gene and acetoacetyl-CoA reductase gene were 1608 bp (536 aa), 1176 bp (392 aa) and 735 bp (245 aa) long, respectively.

EXAMPLE IV

PHA-Producing Recombinant *E. coli* Containing PHA Biosynthesis-Related Genes Derived from *A. latus*

The recombinant expression vector pJC1 anchoring the 6.4 kb genomic DNA fragment of *Alcaligenes latus* was used to transform *E. coli* XL1-Blue. Since the bacteria which took up the recombinant expression vector could grow in a medium containing ampicillin, selection of the *E. coli* transformants was made on a solid medium containing 100 g/ml ampicillin. The selected *E. coli* was cultured in a defined or complex liquid medium containing 20 g/l glucose to produce PHA. When the strain was cultured at a temperature of 30 or 37° C. in a flask, PHA was accumulated until it represented as much as 40% or more of the dry cell weight.

As described hereinbefore, the PHA biosynthesis-related genes of the present invention are derived from *Alcaligenes latus* and contains all of the genes for PHA synthase, β-ketothiolase and acetoacetyl-CoA reductase. When *E. coli* is transformed with the PHA biosynthesis-related genes of the present invention, a one-step culture of the transformant *E. coli* can mass-produce PHA. In addition, these enzymes and the genes are very helpful in understanding the biosynthesis of PHA in a molecular biological level.

The present invention has been described in an illustrative manner, and it is to be understood the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

EXAMPLE V

Separation of the PHA Synthase Gene from *Alcaligenes latus* and Determination of its DNA and Amino Acid Sequence In order to separate out the PHA synthase gene, total DNA was extracted from culture of *Alcaligenes latus* and digested with restriction enzymes such as BamHI, HindIII, SmaI, XhoI, and SalI and the DNA fragment was obtained.

The 3.2 kb DNA fragment showing a positive signal was separated from the fragments resulting from the BamHI digestion by using the 1 kb PHA synthase gene that was derived from *Alcaligenes eutrophus* as a probe.

Then the separated DNA was ligated to the BamHI restriction site of the vector pSK(+), whereby recombinant plasmid pAL32 was constructed. (see FIG. 4)

As the result of analyzing the pAL32 DNA sequence, by the Sanger Method (dideoxy-nucleotide chain termination method), it was revealed that the PHA synthase gene derived from *Alcaligenes latus* consists of 1,608 bp. The amino acid sequence of the PHA synthase encoded by the above PHA synthase gene, was analyzed by using PC/Gene software program. PHA synthase derived from *Alcaligenes latus* has the amino acid sequence composed by 536 amino acids.

EXAMPLE VI

Construction of Recombinant Expression vector pKTC32 Containing the PHA Synthase Gene The PHA synthase gene is obtained by digesting pAL32 with EcoRI and NotI, and then the resulting DNA fragment was ligated to the restriction site by EcoRI and NotI. (see FIG. 4)

EXAMPLE VII

Preparation of PHA-producing Recombinant *Alcaligenes eutrophus* LAR5

The recombinant expression vector pKTC32 of Example VI was introduced into the strains of *A. eutrophus* DSM541 which is lacking in PHA synthase gene. When culturing the transformant, PHB particles in the cell were observed.

EXAMPLE VIII

Identification of Primer Region of a PHA Gene Derived From *A. latus*

For the purpose of identifying the PHA gene primer region, the total DNA of *Alcaligenes latus* was separated. The location of the starting site for RNA transcription was determined by the primer extension method, and then the promoter region consisting of 210 bp DNA upstream was obtained. The gene sequence of promoter region of PHA was analyzed by the PC/Gene software program.

DEPOSIT OF BIOLOGICAL MATERIALS

Deposit No. KCTC 0568 BP

The vector designated as *Alcaligenes eutrophus* LAR5 was deposited in the Korean Collection for Type Cultures (KCTC) of the Korean Research Institute of Bioscience and Biotechnology (KRIBB) International Depository Authority, at #52 Oun-dong, Yusong-ku, Taejon 305–333, Republic of Korea, in compliance with the Budapest Treaty on the International Recognition of the Deposit of Microorganisms for the Purpose of Patent Procedure, on Jan. 18, 1999.

Deposit No. KCTC 0398 BP

The vector designated as *Escherichia coli* XL1-bluepJC1, was deposited in the Korean Collection for Type Cultures (KCTC) of the Korean Research Institute of Bioscience and Biotechnology (KRIBB) International Depository Authority, at #52 Oun-dong, Yusong-ku, Taejon 305–333, Republic of Korea, in compliance with the Budapest Treaty on the International Recognition of the Deposit of Microorganisms for the Purpose of Patent Procedure, on Nov. 5, 1997.

What is claimed:

1. A method for producing polyhydroxyalkanoate (PHA) and its copolymers comprising culturing a host cell transformed with a vector comprising a PHA biosynthesis-related DNA fragment,
wherein said DNA fragment is isolated from *Alcaligenes latus* and comprises three open reading frames operatively connected in the following order from 5' to 3':
   (a) a gene encoding PHA synthase whose protein sequence is set forth in SEQ ID NO:5,
   (b) a gene encoding β-ketothiolase whose protein sequence is set forth in SEQ ID NO:6, and
   (c) a gene encoding acetoacetyl-CoA reductase whose protein sequence is set forth in SEQ ID NO:7.

2. The method as set forth in claim 1, wherein the gene for polyhydroxyalkanoate synthase has the base sequence shown in SEQ ID NO:2.

3. The method as set forth in claim 1 wherein the gene for β-ketothiolase has the base sequence shown in SEQ ID NO:3.

4. The method as set forth in claim 1, wherein the gene for acetoacetyl-CoA reductase has the base sequence shown in SEQ ID NO:4.

5. The method as set forth in claim 1, wherein the polyhydroxyalkanoate biosynthesis-related DNA fragment has the base sequence shown in SEQ ID NO:1.

6. The method as set forth in claim 1, wherein the vector is an expression vector comprising an expression control sequence operatively linked to the polyhydroxyalkanoate biosynthesis-related DNA fragment.

7. The method as set forth in claim 1, wherein the vector is pJC1.

8. The method as set forth in claim 1, wherein the host cell is a prokaryote.

9. The method as set forth in claim 8, wherein the host cell is an *E. coli*.

10. The method as set forth in claim 1, wherein the host cell is *E. coli* transformant XL1-Blue/pJC1 deposited as KCTC 0398BP.

11. A method for producing polyhydroxyalkanoate and its copolymers, by culturing a host cell transformed with pKTC32.

12. A method for producing polyhydroxyalkanoate and its copolymers, by culturing an *Alcaligenes eutropus* deposited as KCTC 0568BP.

* * * * *

SEQUENCE LISTING

<160> NUMBER OF SEQ ID NOS: 8

<210> SEQ ID NO 1
<211> LENGTH: 6436
<212> TYPE: DNA
<213> ORGANISM: Alcaligenes latus
<220> FEATURE:
<221> NAME/KEY: gene
<222> LOCATION: (1)..(6436)
<223> OTHER INFORMATION: double stranded linear oligonucleotide for
      polyhydroxyalkanoate biosynthesis-related genes

<400> SEQUENCE: 1

```
ggatcctgct gcgctcggac aaaagcatgg gccgagttta gcgcgcgccc tcggacgccc        60
ccggcagcgt gcagggttca cgccatgttc aaaagcgctg tgaggcaggt atgctgcact       120
gcgtcaatcc cgcagttccg cagtcatccc agaaatgcag ctgtacaact actttcgctc       180
ctcggcgtcc taccgcgtcc gcatcgcact ggccctgaag ggtctggcct acgaatacaa       240
gccggtgcac ctgcagaaga aggagcagtt cgcggagtcg tatgcggccg tgtcggcctc       300
gcgcctggtg ccgctgctgc gcgacggcga cgcgtcgctg acgcagtcga tggccatcat       360
cgagtacctg gacgagaccc atccgcagcc gccgctgctg ccctcggacc cgctgggccg       420
cgcccgcgtg cgtgcgctgg cgcaggacat cgcctgcgag atccaccgc  tcaacaacct       480 gcgcgtgctg cgctacctgg cgcacgacct caaggtcggc gaggacgaca agaaccgctg       540
gtaccgccac tgggtcgaga ccggcctgga ggtggtggag cgccagctgg cggatcaccc       600
gtccaccggc cgcttctgcc atggcgacac gcccggcctg gccgattgcg tgctggtgcc       660
gcagatcttc aacgcccagc gtttcaactg ccggctggag cacgtgccca ccgtgatgcg       720
cgtgtacgag gcctgcatgc agctcgacgc cttcgacaag acgcagccct ccgcctgtcc       780
cgatgccgag taaggctctg cagggcgtgc tgaggcccga gtggccggca ccggccggcg       840
tgggcgcatt catgagcacg cgcgagggcg gcgtcagcgc cgcgccctgg gacgcgccca       900
acctgggcga cgccgtgggc gacagcccgc aggctgtgga caccaaccgc gcccgattcg       960
ccgccgccgc cgagggcggc acgccggtgt ggctgcgcca ggtccacggc acgcgggtgc      1020
tgcgattgcg cgccggcgag gccttgccgg cgcagccgcc cgaggccgat gccgtggtca      1080
ccgccgaccc cggcctggtg tgcgtggtgc aggtggcgga ctgcctgccc gtgttcttcg      1140
cagcgtccaa cggccgtgcc gtcggcgctg cgcatgcggg ctggcgcggc ctggccggtg      1200
gcgtgctcga aaacacgctg gccgaggtgt gcgcgctggc gcgctgcgag ccctccgatg      1260
tgctggcctg gatggggccc tgcatcgggc cggagagttt cgaggtgggg cgcgacgtgc      1320
tggagggttt cggcgtggat ccggacggtc cggccgaccc ggccttcgcc tggcgtccgc      1380
gtgccgacgg cagcgcgcgc tggctggcgg acctgccggg gctggcgcgg cgccggctcg      1440
aattggcagg tctgcgtcag atcagtggcg gacagtggtg cacggtgcag gatcgttcac      1500
ggttcttctc gttccggcgg gaccgggtca cggggcggca ggctgccgcc gtctggctgc      1560
gcggatgaag cggtgtcctc ggcgcgcttg cgcgcccgtc gccgcgccgg cgtccccagg      1620
aagtacagga cgatggacaa gggcagtacg ccatacagca gcagcgtgaa caccgcgccg      1680
agcaaggtgc cgttgggcgc catggcttcg gccacggcca tcatcagcac cacgtacagc      1740
catgccgaga caaccaagta catagcaaaa cccgcaattt cgcagaatg  acgtatttcg      1800 tacaatgaaa actgttgtca tgatgcggta agacacgaag cctacaacgc gatccagcaa      1860
```

-continued

```
cggttttcgt gaaaaagtcc tcaggagacg agcgtgacac tgcatcccat tcccgcactg    1920
caacagcttg gcgacaacgc cacggcgctg agtgccgcca tctcggaagc gctgcgcgcg    1980
atgtcgggcc tgaacctgcc gatgcaggcc atgaccaagc tgcagggcga gtacctcaac    2040
gaggcgacgg cgctgtggaa ccagacgctg ggccgcctgc agcccgacgg cagcgcccaa    2100
ccggccaagc tgggcgaccg cgcgcttctcg gccgaggact gggccaagaa ccccgccgcg    2160
gcctacctgg cgcaggtcta cctgctcaat gcccgcacgc tgatgcagat ggccgagtcc    2220
atcgagggcg acgccaaggc caaggcgcgc gtgcgcttcg ccgtgcagca gtggatcgac    2280
gccgcggcgc cgagcaactt cctggcgctc aatcccgagg cgcagcgcaa ggcgctggag    2340
accaaggggg agagcatcag ccagggcctg cagcagctgt ggcatgacat ccagcagggc    2400
cacgtgtcgc agacggacga gagcgtgttc gaggtgggca agaacgtcgc caccaccgag    2460
ggcgcggtcg tgtacgagaa cgacctgttc cagctcatcg agtacaagcc gctgacgccc    2520
aaggtgcacg agaagccgat gctgttcgtg ccgccgtgca tcaacaagta ctacatcctg    2580
gacctgcagc cggacaacag cctcatccgc tacaccgtcg cccagggcca ccgggtgttc    2640
gtggtgagct ggcgcaaccc cgacgcctcc gtcgccggca agacctggga cgactacgtg    2700
gagcagggcg tgatccgcgc catccgcgtg atgcagcaga tcacggggca cgagaaggtc    2760
aacgcgctgg gcttctgcgt cggcggcacc atcctgagca cggcgctggc ggtgctggcc    2820
gcgcgcggcg agcagcccgc ggcgagcctg acgctgctga ccacgctgct ggacttcagc    2880
aacaccggcg tgctggacct gttcatcgac gaggccggcg tgcgcctgcg cgagatgacc    2940
atcggcgaga aggcgcccaa cggcccgggc ctgctcaacg gcaaggagct ggccaccacc    3000
ttcagcttcc tgcgcccgaa cgacctggtc tggaactacg tggtgggcaa ctacctcaag    3060
ggcgaggcgc cgccgccctt cgacctgctg tactggaact ccgacagcac caacatggcc    3120
gggcccatgt tctgctggta cctgcgcaac acctacctgg agaacaagtt gcgcgttccc    3180
ggtgccctga ccatctgcgg cgagaaggtg gacctctcgc gcatcgaggc gccggtgtac    3240
ttctacggtt cgcgcgagga ccacatcgtg ccctgggaat cggcctacgc cggcacgcag    3300
atgctgagcg gccccaagcg ctatgtcctg ggtgcgtctg gccacatcgc cggcgtgatc    3360
aaccccccgc agaagaagaa gcgcagctac tggaccaacg agcagctcga cggcgacttc    3420
aaccagtggc tggaaggctc caccgagcat cctggcagct ggtggaccga ctggagcgac    3480
tggctcaagc agcacgcggg caaggaaatc gccgcaccca agactcccgg caacaagacc    3540
cacaagccca tcgagcccgc ccccgggcgt tacgtgaagc agaaggcctg agccgcggcc    3600
cctgagcctt ctttaacccg accttgacaa acgaggagat aagcatgacc gacatcgtca    3660
tcgtcgccgc agcccgcacc gccgtgggca agttcggcgg cacgctggcc aagacccccg    3720
ctccggagct gggcgccgtg gtcatcaagg ccctgctgga agacgggca gtcaagcccg    3780
accagatcgg tgaagtcatc atgggccagg tgctggccgc cggcgcgggc cagaaccccg    3840
cgcgccaggc gatgatgaag gcgggcatcg ccaaggaaac gccggcgctg accatcaacg    3900
ccgtgtgcgg ctccggcctc aaggccgtga tgctggccgc ccaggccatc gcctggggcg    3960
acagcgacat cgtcatcgcc ggcggccagg agaacatgag cgccagcccg cacgtgctga    4020
tgggcagccg cgacggccag cgcatgggcg actggaagat ggtcgacacc atgatcaacg    4080
acggcctgtg ggacgtgtac aacaagtacc acatgggcat cacggccgag aacgtcgcca    4140
aggaacacga catcagccgc gaccagcagg acgccctggc cctggccagc cagcagaagg    4200
ccaccgccgc gcaggaagcc ggccgcttca aggacgagat cgttccggtc tcgatcccgc    4260
```

```
agcgcaaggg cgacccggtg ctgttcgaca ccgacgagtt catcaacaag aagaccaccg    4320
ccgaagcgct ggcgggcctg cgcccggcct tcgacaaggc cggcagcgtg accgcgggca    4380
acgcctcggg catcaacgac ggcgccgctg cggtgatggt gatgtccgcc gccaaggcga    4440
aggagctggg cctgacgccc atggcgcgca tcaagagctt cggcaccagc ggcctggatc    4500
cggccaccat gggcatgggc ccggtgccgg cctcgcgcaa ggcgctggag cgcgccggct    4560
ggcaggtcgg tgacgtggac ctgttcgagc tcaacgaagc cttcgccgcc caggcctgcg    4620
cggtgaacaa ggagctgggc gtggatccgg ccaaggtcaa cgtcaacggc ggtgccatcg    4680
ccatcggcca ccccatcggc gcctccggct gccgcgtgct ggtgacgctg ctgcacgaga    4740
tgcagcgccg ggacgccaag aagggcctgg ccgcgctgtg catcggcggc ggcatgggcg    4800
tgtcgctgac cgtcgagcgc tgatcagaag aaccgggcgg ccccgcgccg cccgcccggc    4860
gttccacgcg ggtgcgccgg gataccagac gaaccaaacc accaagggct tcgagacggc    4920
ccgaagaagg agagacagat ggcacagaaa ctggcttacg tgaccggcgg catgggcggc    4980
atcggcacct cgatgtgcca gcgcctgcac aaggacggct tcaaggtgat cgccggctgc    5040
ggtccgagcc gcgaccacca gaagtggatc gatgaacagg ccgcgctggg ctataccttc    5100
tacgcctccg tgggcaacgt ggccgactgg gactccaccg tggccgcctt cgagaaggtc    5160
aaggccgagc acggcaccgt ggacgtgctg gtgaacaacg ccggcatcac gcgtgacggg    5220
cagttccgca agatgagcaa ggccgattgg caggccgtga tgtcgaccaa cctcgacagc    5280
atgttcaacg tcaccaagca ggtgatcgag ggcatgctgg acaagggctg gggccggatc    5340
atcaacatct cctcggtcaa cggcgagaag gccagttcg ccagaccaa ctactccgcc    5400 gccaaggccg gcatgcacgg cttctcgatg gcgctggcgc aggaagtggc ggccaagggc    5460
gtgacggtga acaccgtgag cccgggctac atcgccacgg acatggtcaa ggccatccgc    5520
caggacgtgc tggacaagat catcgccacc attcccatcc gtcgcctggg tacgccggag    5580
gagatcgcct ccatcgtcgc ctggctggcc ggcgaggagt cgggcttcac caccggtgcc    5640
gacttcagct gcaacggcgg cctgcacatg ggctgaggcc cgcggctcca tgcccacctg    5700
cgtgggcatg gacgggccga aggacccgag ctctgcgagg gtgcggcctg caaggctgag    5760
gcctgctgcg ccgcgtgccc gcgagggcac gtgccgaagc accaaaaggc cgcgcattgc    5820
gcggcctttt cctttctgga tcggtgcgga cgggtgccgc gtcaggcagg cagggcccc    5880 cgggccttca ctccaccatg cccgacatga agtacttgat cagccccttg ccgcgaagc    5940 ccagcatgcc gaagcccagc gccaggaaca gcacgaaggt gccgaacttg ccggccttcg    6000
actcgcgcgc gagctgaaag atgatgaatg ccatgtagac catgaaggcc gtgacgccga    6060
cggtcaggcc cagctgggca atgttttcct cgttgatttc gaacatcgtt tgttgtctca    6120
ggctgctgca cgcggctgac gtgctcgccg cgcggccggg ccccaactgc ccgcagcggt    6180
tctcgatcag gttctcaagg catctcgtgc cactgggagg tgtccaccag gtcgcggtag    6240
gcgtgccagc tcgaatgcgc cagccacggc actaccacga tcaggcccag cagcagcgtg    6300
gccatgccca gcagcgtcag cgccatgatc agcgccgccc acagcgccag cggcagtggg    6360
tgctgcatca ccacgcgcca gctcgtgagc accgccacca gcacgccac gtggcggtcc    6420 agcagcatcg ggatcc                                                    6436
```

<210> SEQ ID NO 2  
<211> LENGTH: 1611  
<212> TYPE: DNA

<213> ORGANISM: Alcaligenes latus
<220> FEATURE:
<221> NAME/KEY: gene
<222> LOCATION: (1)..(1611)
<223> OTHER INFORMATION: double stranded linear oligonucleotide for
      polyhydroxyalkanoate synthase

<400> SEQUENCE: 2

| | | | | | |
|---|---|---|---|---|---|
| atgtcgggcc | tgaacctgcc | gatgcaggcc | atgaccaagc | tgcaggcgga | gtacctcaac | 60 |
| gaggcgacgg | cgctgtggaa | ccagacgctg | ggccgcctgc | agcccgacgg | cagcgcccaa | 120 |
| ccggccaagc | tgggcgaccg | cgcttctcg | gccgaggact | gggccaagaa | ccccgccgcg | 180 |
| gcctacctgg | cgcaggtcta | cctgctcaat | gcccgcacgc | tgatgcagat | ggccgagtcc | 240 |
| atcgagggca | cgccaaggc | caaggcgcgc | gtgcgcttcg | ccgtgcagca | gtggatcgac | 300 |
| gccgcggcgc | cgagcaactt | cctggcgctc | aatcccgagg | cgcagcgcaa | ggcgctggag | 360 |
| accaaggggg | agagcatcag | ccagggcctg | cagcagctgt | ggcatgacat | ccagcagggc | 420 |
| cacgtgtcgc | agacggacga | gagcgtgttc | gaggtgggca | agaacgtcgc | caccaccgag | 480 |
| ggcgcggtcg | tgtacgagaa | cgacctgttc | cagctcatcg | agtacaagcc | gctgacgccc | 540 |
| aaggtgcacg | agaagccgat | gctgttcgtg | ccgccgtgca | tcaacaagta | ctacatcctg | 600 |
| gacctgcagc | cggacaacag | cctcatccgc | tacaccgtcg | cccagggcca | ccgggtgttc | 660 |
| gtggtgagct | ggcgcaaccc | cgacgcctcc | gtcgccggca | agacctggga | cgactacgtg | 720 |
| gagcagggcg | tgatccgcgc | catccgcgtg | atgcagcaga | tcacgggca | cgagaaggtc | 780 |
| aacgcgctgg | gcttctgcgt | cggcggcacc | atcctgagca | cggcgctggc | ggtgctggcc | 840 |
| gcgcgcggcg | agcagcccgc | ggcgagcctg | acgctgctga | ccacgctgct | ggacttcagc | 900 |
| aacaccggcg | tgctggacct | gttcatcgac | gaggccggcg | tgcgcctgcg | cgagatgacc | 960 |
| atcggcgaga | aggcgcccaa | cggcccgggc | ctgctcaacg | gcaaggagct | ggccaccacc | 1020 |
| ttcagcttcc | tgcgcccgaa | cgacctggtc | tggaactacg | tggtgggcaa | ctacctcaag | 1080 |
| ggcgaggcgc | cgccgccctt | cgacctgctg | tactggaact | ccgacagcac | caacatggcc | 1140 |
| gggcccatgt | tctgctggta | cctgcgcaac | acctacctgg | agaacaagtt | gcgcgttccc | 1200 |
| ggtgccctga | ccatctgcgg | cgagaaggtg | gacctctcgc | gcatcgaggc | gccggtgtac | 1260 |
| ttctacggtt | cgcgcgagga | ccacatcgtg | ccctgggaat | cggcctacgc | cggcacgcag | 1320 |
| atgctgagcg | gccccaagcg | ctatgtcctg | ggtgcgtctg | gccacatcgc | cggcgtgatc | 1380 |
| aacccccgc | agaagaagaa | gcgcagctac | tggaccaaca | gcagctcga | cggcgacttc | 1440 |
| aaccagtggc | tggaaggctc | caccgagcat | cctggcagct | ggtggaccga | ctggagcgac | 1500 |
| tggctcaagc | agcacgcggg | caaggaaatc | gccgcaccca | agactcccgg | caacaagacc | 1560 |
| cacaagccca | tcgagcccgc | ccccgggcgt | tacgtgaagc | agaaggcctg | a | 1611 |

<210> SEQ ID NO 3
<211> LENGTH: 1179
<212> TYPE: DNA
<213> ORGANISM: Alcaligenes latus
<220> FEATURE:
<221> NAME/KEY: gene
<222> LOCATION: (1)..(1179)
<223> OTHER INFORMATION: double stranded linear oligonucleotide for
      beta-ketothiolase

<400> SEQUENCE: 3

| | | | | | |
|---|---|---|---|---|---|
| atgaccgaca | tcgtcatcgt | cgccgcagcc | cgcaccgccg | tgggcaagtt | cggcggcacg | 60 |
| ctggccaaga | cccccgctcc | ggagctgggc | gccgtggtca | tcaaggccct | gctggagaag | 120 |

```
acgggcgtca agcccgacca gatcggtgaa gtcatcatgg gccaggtgct ggccgccggc    180
gcgggccaga accccgcgcg ccaggcgatg atgaaggcgg gcatcgccaa ggaaacgccg    240
gcgctgacca tcaacgccgt gtgcggctcc ggcctcaagg ccgtgatgct ggccgcccag    300
gccatcgcct ggggcgacag cgacatcgtc atcgccggcg gccaggagaa catgagcgcc    360
agcccgcacg tgctgatggg cagccgcgac ggccagcgca tgggcgactg gaagatggtc    420
gacaccatga tcaacgacgg cctgtgggac gtgtacaaca agtaccacat gggcatcacg    480
gccgagaacg tcgccaagga acacgacatc agccgcgacc agcaggacgc cctggccctg    540
gccagccagc agaaggccac cgccgcgcag gaagccggcc gcttcaagga cgagatcgtt    600
ccggtctcga tcccgcagcg caagggcgac ccggtgctgt cgacaccga cgagttcatc     660 aacaagaaga ccaccgccga agcgctggcg ggcctgcgcc cggccttcga caaggccggc    720
agcgtgaccg cgggcaacgc ctcgggcatc aacgacggcg ccgctgcggt gatggtgatg    780
tccgccgcca aggcgaagga gctgggcctg acgcccatgg cgcgcatcaa gagcttcggc    840
accagcggcc tggatccggc caccatgggc atgggcccgg tgccggcctc gcgcaaggcg    900
ctggagcgcg ccggctggca ggtcggtgac gtggacctgt cgagctcaa cgaagccttc     960 gccgcccagg cctgcgcggt gaacaaggag ctgggcgtgg atccggccaa ggtcaacgtc   1020
aacggcggtg ccatcgccat cggccacccc atcggcgcct ccggctgccg cgtgctggtg   1080
acgctgctgc acgagatgca gcgccgggac gccaagaagg gcctggccgc gctgtgcatc   1140
ggcggcggca tgggcgtgtc gctgaccgtc gagcgctga                           1179

<210> SEQ ID NO 4
<211> LENGTH: 738
<212> TYPE: DNA
<213> ORGANISM: Alcaligenes latus
<220> FEATURE:
<221> NAME/KEY: gene
<222> LOCATION: (1)..(738)
<223> OTHER INFORMATION: double stranded linear oligonucleotide for
      acetoacetyl-CoA reductase

<400> SEQUENCE: 4
atggcacaga aactggctta cgtgaccggc ggcatgggcg gcatcggcac ctcgatgtgc     60
cagcgcctgc acaaggacgg cttcaaggtg atcgccggct gcggtccgag ccgcgaccac    120
cagaagtgga tcgatgaaca ggccgcgctg ggctatacct tctacgcctc cgtgggcaac    180
gtggccgact gggactccac cgtggccgcc ttcgagaagg tcaaggccga gcacggcacc    240
gtggacgtgc tggtgaacaa cgccggcatc acgcgtgacg ggcagttccg caagatgagc    300
aaggccgatt ggcaggccgt gatgtcgacc aacctcgaca gcatgttcaa cgtcaccaag    360
caggtgatcg agggcatgct ggacaagggc tggggccgga tcatcaacat ctcctcgggtc   420 aacggcgaga agggccagtt cggccagacc aactactccg ccgccaaggc cggcatgcac    480
ggcttctcga tggcgctggc gcaggaagtg cggccaagg gcgtgacggt gaacaccgtg     540
agcccgggct acatcgccac ggacatggtc aaggccatcc gccaggacgt gctggacaag    600
atcatcgcca ccattcccat ccgtcgcctg ggtacgccgg aggagatcgc ctccatcgtc    660
gcctggctgg ccggcgagga gtcgggcttc accaccggtg ccgacttcag ctgcaacggc    720
ggcctgcaca tgggctga                                                  738

<210> SEQ ID NO 5
<211> LENGTH: 536
```

-continued

```
<212> TYPE: PRT
<213> ORGANISM: Alcaligenes latus
<220> FEATURE:
<221> NAME/KEY: PEPTIDE
<222> LOCATION: (1)..(536)
<223> OTHER INFORMATION: polyhydroxyalkanoate synthase

<400> SEQUENCE: 5
```

Met Ser Gly Leu Asn Leu Pro Met Gln Ala Met Thr Lys Leu Gln Gly
 1               5                  10                  15

Glu Tyr Leu Asn Glu Ala Thr Ala Leu Trp Asn Gln Thr Leu Gly Arg
            20                  25                  30

Leu Gln Pro Asp Gly Ser Ala Gln Pro Ala Lys Leu Gly Asp Arg Arg
        35                  40                  45

Phe Ser Ala Glu Asp Trp Ala Lys Asn Pro Ala Ala Tyr Leu Ala
    50                  55                  60

Gln Val Tyr Leu Leu Asn Ala Arg Thr Leu Met Gln Met Ala Glu Ser
 65                  70                  75                  80

Ile Glu Gly Asp Ala Lys Ala Lys Ala Arg Val Arg Phe Ala Val Gln
                85                  90                  95

Gln Trp Ile Asp Ala Ala Pro Ser Asn Phe Leu Ala Leu Asn Pro
            100                 105                 110

Glu Ala Gln Arg Lys Ala Leu Glu Thr Lys Gly Glu Ser Ile Ser Gln
        115                 120                 125

Gly Leu Gln Gln Leu Trp His Asp Ile Gln Gly His Val Ser Gln
    130                 135                 140

Thr Asp Glu Ser Val Phe Glu Val Gly Lys Asn Val Ala Thr Thr Glu
145                 150                 155                 160

Gly Ala Val Val Tyr Glu Asn Asp Leu Phe Gln Leu Ile Glu Tyr Lys
                165                 170                 175

Pro Leu Thr Pro Lys Val His Glu Lys Pro Met Leu Phe Val Pro Pro
            180                 185                 190

Cys Ile Asn Lys Tyr Tyr Ile Leu Asp Leu Gln Pro Asp Asn Ser Leu
        195                 200                 205

Ile Arg Tyr Thr Val Ala Gln Gly His Arg Val Phe Val Val Ser Trp
    210                 215                 220

Arg Asn Pro Asp Ala Ser Val Ala Gly Lys Thr Trp Asp Asp Tyr Val
225                 230                 235                 240

Glu Gln Gly Val Ile Arg Ala Ile Arg Val Met Gln Gln Ile Thr Gly
                245                 250                 255

His Glu Lys Val Asn Ala Leu Gly Phe Cys Val Gly Gly Thr Ile Leu
            260                 265                 270

Ser Thr Ala Leu Ala Val Leu Ala Ala Arg Gly Glu Gln Pro Ala Ala
        275                 280                 285

Ser Leu Thr Leu Leu Thr Thr Leu Leu Asp Phe Ser Asn Thr Gly Val
    290                 295                 300

Leu Asp Leu Phe Ile Asp Glu Ala Gly Val Arg Leu Arg Glu Met Thr
305                 310                 315                 320

Ile Gly Glu Lys Ala Pro Asn Gly Pro Gly Leu Leu Asn Gly Lys Glu
                325                 330                 335

Leu Ala Thr Thr Phe Ser Phe Leu Arg Pro Asn Asp Leu Val Trp Asn
            340                 345                 350

Tyr Val Val Gly Asn Tyr Leu Lys Gly Glu Ala Pro Pro Pro Phe Asp
        355                 360                 365

Leu Leu Tyr Trp Asn Ser Asp Ser Thr Asn Met Ala Gly Pro Met Phe

-continued

```
                370                 375                 380
Cys Trp Tyr Leu Arg Asn Thr Tyr Leu Glu Asn Lys Leu Arg Val Pro
385                 390                 395                 400

Gly Ala Leu Thr Ile Cys Gly Glu Lys Val Asp Leu Ser Arg Ile Glu
                405                 410                 415

Ala Pro Val Tyr Phe Tyr Gly Ser Arg Glu Asp His Ile Val Pro Trp
                420                 425                 430

Glu Ser Ala Tyr Ala Gly Thr Gln Met Leu Ser Gly Pro Lys Arg Tyr
                435                 440                 445

Val Leu Gly Ala Ser Gly His Ile Ala Gly Val Ile Asn Pro Pro Gln
                450                 455                 460

Lys Lys Lys Arg Ser Tyr Trp Thr Asn Glu Gln Leu Asp Gly Asp Phe
465                 470                 475                 480

Asn Gln Trp Leu Glu Gly Ser Thr Glu His Pro Gly Ser Trp Trp Thr
                485                 490                 495

Asp Trp Ser Asp Trp Leu Lys Gln His Ala Gly Lys Glu Ile Ala Ala
                500                 505                 510

Pro Lys Thr Pro Gly Asn Lys Thr His Lys Pro Ile Glu Pro Ala Pro
                515                 520                 525

Gly Arg Tyr Val Lys Gln Lys Ala
                530                 535

<210> SEQ ID NO 6
<211> LENGTH: 392
<212> TYPE: PRT
<213> ORGANISM: Alcaligenes latus
<220> FEATURE:
<221> NAME/KEY: PEPTIDE
<222> LOCATION: (1)..(392)
<223> OTHER INFORMATION: beta-ketothiolase

<400> SEQUENCE: 6

Met Thr Asp Ile Val Ile Val Ala Ala Ala Arg Thr Ala Val Gly Lys
 1               5                  10                  15

Phe Gly Gly Thr Leu Ala Lys Thr Pro Ala Pro Glu Leu Gly Ala Val
                20                  25                  30

Val Ile Lys Ala Leu Leu Glu Lys Thr Gly Val Lys Pro Asp Gln Ile
            35                  40                  45

Gly Glu Val Ile Met Gly Gln Val Leu Ala Ala Gly Ala Gly Gln Asn
        50                  55                  60

Pro Ala Arg Gln Ala Met Met Lys Ala Gly Ile Ala Lys Glu Thr Pro
65                  70                  75                  80

Ala Leu Thr Ile Asn Ala Val Cys Gly Ser Gly Leu Lys Ala Val Met
                85                  90                  95

Leu Ala Ala Gln Ala Ile Ala Trp Gly Asp Ser Asp Ile Val Ile Ala
                100                 105                 110

Gly Gly Gln Glu Asn Met Ser Ala Ser Pro His Val Leu Met Gly Ser
            115                 120                 125

Arg Asp Gly Gln Arg Met Gly Asp Trp Lys Met Val Asp Thr Met Ile
        130                 135                 140

Asn Asp Gly Leu Trp Asp Val Tyr Asn Lys Tyr His Met Gly Ile Thr
145                 150                 155                 160

Ala Glu Asn Val Ala Lys Glu His Asp Ile Ser Arg Asp Gln Gln Asp
                165                 170                 175

Ala Leu Ala Leu Ala Ser Gln Gln Lys Ala Thr Ala Ala Gln Glu Ala
                180                 185                 190
```

```
Gly Arg Phe Lys Asp Glu Ile Val Pro Val Ser Ile Pro Gln Arg Lys
            195                 200                 205

Gly Asp Pro Val Leu Phe Asp Thr Asp Glu Phe Ile Asn Lys Lys Thr
        210                 215                 220

Thr Ala Glu Ala Leu Ala Gly Leu Arg Pro Ala Phe Asp Lys Ala Gly
225                 230                 235                 240

Ser Val Thr Ala Gly Asn Ala Ser Gly Ile Asn Asp Gly Ala Ala Ala
                245                 250                 255

Val Met Val Met Ser Ala Ala Lys Ala Lys Glu Leu Gly Leu Thr Pro
                260                 265                 270

Met Ala Arg Ile Lys Ser Phe Gly Thr Ser Gly Leu Asp Pro Ala Thr
            275                 280                 285

Met Gly Met Gly Pro Val Pro Ala Ser Arg Lys Ala Leu Glu Arg Ala
        290                 295                 300

Gly Trp Gln Val Gly Asp Val Asp Leu Phe Glu Leu Asn Glu Ala Phe
305                 310                 315                 320

Ala Ala Gln Ala Cys Ala Val Asn Lys Glu Leu Gly Val Asp Pro Ala
                325                 330                 335

Lys Val Asn Val Asn Gly Gly Ala Ile Ala Ile Gly His Pro Ile Gly
                340                 345                 350

Ala Ser Gly Cys Arg Val Leu Val Thr Leu Leu His Glu Met Gln Arg
            355                 360                 365

Arg Asp Ala Lys Lys Gly Leu Ala Ala Leu Cys Ile Gly Gly Gly Met
        370                 375                 380

Gly Val Ser Leu Thr Val Glu Arg
385                 390

<210> SEQ ID NO 7
<211> LENGTH: 245
<212> TYPE: PRT
<213> ORGANISM: Alcaligenes latus
<220> FEATURE:
<221> NAME/KEY: PEPTIDE
<222> LOCATION: (1)..(245)
<223> OTHER INFORMATION: acetoacetyl-CoA reductase

<400> SEQUENCE: 7

Met Ala Gln Lys Leu Ala Tyr Val Thr Gly Gly Met Gly Gly Ile Gly
 1               5                  10                  15

Thr Ser Met Cys Gln Arg Leu His Lys Asp Gly Phe Lys Val Ile Ala
            20                  25                  30

Gly Cys Gly Pro Ser Arg Asp His Gln Lys Trp Ile Asp Glu Gln Ala
        35                  40                  45

Ala Leu Gly Tyr Thr Phe Tyr Ala Ser Val Gly Asn Val Ala Asp Trp
    50                  55                  60

Asp Ser Thr Val Ala Ala Phe Glu Lys Val Lys Ala Glu His Gly Thr
65                  70                  75                  80

Val Asp Val Leu Val Asn Asn Ala Gly Ile Thr Arg Asp Gly Gln Phe
                85                  90                  95

Arg Lys Met Ser Lys Ala Asp Trp Gln Ala Val Met Ser Thr Asn Leu
            100                 105                 110

Asp Ser Met Phe Asn Val Thr Lys Gln Val Ile Glu Gly Met Leu Asp
        115                 120                 125

Lys Gly Trp Gly Arg Ile Ile Asn Ile Ser Ser Val Asn Gly Glu Lys
    130                 135                 140
```

```
Gly Gln Phe Gly Gln Thr Asn Tyr Ser Ala Ala Lys Ala Gly Met His
145                 150                 155                 160

Gly Phe Ser Met Ala Leu Ala Gln Glu Val Ala Ala Lys Gly Val Thr
            165                 170                 175

Val Asn Thr Val Ser Pro Gly Tyr Ile Ala Thr Asp Met Val Lys Ala
            180                 185                 190

Ile Arg Gln Asp Val Leu Asp Lys Ile Ile Ala Thr Ile Pro Ile Arg
        195                 200                 205

Arg Leu Gly Thr Pro Glu Glu Ile Ala Ser Ile Val Ala Trp Leu Ala
        210                 215                 220

Gly Glu Glu Ser Gly Phe Thr Thr Gly Ala Asp Phe Ser Cys Asn Gly
225                 230                 235                 240

Gly Leu His Met Gly
                245

<210> SEQ ID NO 8
<211> LENGTH: 315
<212> TYPE: DNA
<213> ORGANISM: Alcaligenes latus
<220> FEATURE:
<221> NAME/KEY: promoter
<222> LOCATION: (1)..(315)
<223> OTHER INFORMATION: single stranded linear oligonucleotide for
      promoter gene

<400> SEQUENCE: 8
acaccgcgcc gagcaaggtg ccgttgggcg ccatggcttc ggccacggcc atcatcagca         60
ccacgtaaca gccatgccag agcaaccaag tacatagcaa aaacccgcaa ttacgcagaa        120
tgacgtattt cgtacaatga aaactgttgt catgatgcgg taagacacga agcctacaac        180
gcgatccagc aacggttttc gtgaaaaagt cctcaggaga cgagcgtgac actgcaaatc        240
ccattcccgc actgcaacag cttggcgaca acgccacggc gctgagtgcc gccatctggg        300
aacgtgcgcg cgatg                                                        315
```